US012479702B2

(12) United States Patent
Huang et al.

(10) Patent No.: US 12,479,702 B2
(45) Date of Patent: Nov. 25, 2025

(54) AUTOMATIC CONVEYOR AND AUTOMATIC CLEANING DEVICE FOR THE HANDRAIL BELT THEREOF

(71) Applicant: Otis Elevator Company, Farmington, CT (US)

(72) Inventors: Jiangxing Huang, Hangzhou (CN); Zhengguang Zhou, Hangzhou (CN); Mingli Zhou, Hangzhou (CN); Minglei Feng, Hangzhou (CN)

(73) Assignee: OTIS ELEVATOR COMPANY, Farmington, CT (US)

( * ) Notice: Subject to any disclaimer, the term of this patent is extended or adjusted under 35 U.S.C. 154(b) by 138 days.

(21) Appl. No.: 18/365,444

(22) Filed: Aug. 4, 2023

(65) Prior Publication Data

US 2024/0158207 A1 May 16, 2024

(30) Foreign Application Priority Data

Nov. 10, 2022 (CN) ........................ 202211404390.X

(51) Int. Cl.
*B66B 31/02* (2006.01)
*A61L 2/10* (2006.01)
(Continued)

(52) U.S. Cl.
CPC ................ *B66B 31/02* (2013.01); *A61L 2/10* (2013.01); *B08B 1/143* (2024.01); *B08B 1/20* (2024.01);
(Continued)

(58) Field of Classification Search
CPC ....... B66B 31/02; B66B 23/24; B66B 31/003; A61L 2/10; A61L 2202/11;
(Continued)

(56) References Cited

U.S. PATENT DOCUMENTS 5,117,968 A * 6/1992 Rivera .................. B65G 45/18 198/496
10,072,795 B2 * 9/2018 Dlouhy .................. F16N 23/00
(Continued)

FOREIGN PATENT DOCUMENTS

CN 102134039 A * 7/2011 ............ B66B 31/02
DE 2505874 A1 * 8/1976
(Continued)

OTHER PUBLICATIONS

IPSearch History Jul. 18, 2025 UTC; InnovationQ+; https://iq.ip.com/discover (Year: 2025).*

*Primary Examiner* — Gene O Crawford
*Assistant Examiner* — Abby A Jorgensen
(74) *Attorney, Agent, or Firm* — CANTOR COLBURN LLP

(57) ABSTRACT

An automatic conveying device and an automatic cleaning device for the handrail belt thereof. The automatic cleaning device includes a base; a first cleaning unit and a second cleaning unit mounted on the base, the first cleaning unit and the second cleaning unit are arranged in a front and back way in a moving direction of the handrail belt; a cleaning liquid conveying device, for conveying cleaning liquid to the first cleaning unit or the second cleaning unit; and a controller configured to control the cleaning liquid conveying device to deliver the cleaning liquid to one of the first cleaning unit and the second cleaning unit that first comes into contact with the handrail belt based on the running direction of the handrail belt during the cleaning operation.

13 Claims, 3 Drawing Sheets

(51) Int. Cl.
*B08B 1/14* (2024.01)
*B08B 1/20* (2024.01)
*B08B 3/04* (2006.01)
*B08B 13/00* (2006.01)

(52) U.S. Cl.
CPC .............. *B08B 3/041* (2013.01); *B08B 13/00* (2013.01); *A61L 2202/11* (2013.01); *A61L 2202/14* (2013.01); *A61L 2202/17* (2013.01)

(58) Field of Classification Search
CPC . A61L 2202/14; A61L 2202/17; B08B 1/143; B08B 1/20; B08B 3/041; B08B 13/00
See application file for complete search history.

(56) References Cited

U.S. PATENT DOCUMENTS

| | | | | |
|---|---|---|---|---|
| 12,024,401 | B2 * | 7/2024 | Park | B08B 1/34 |
| 2023/0117313 | A1 * | 4/2023 | Wang | B66B 23/06 198/335 |

FOREIGN PATENT DOCUMENTS

| | | | | | |
|---|---|---|---|---|---|
| KR | 100947368 | B1 | * | 3/2010 | B66B 31/02 |
| KR | 20110016145 | A | * | 2/2011 | B66B 31/02 |
| KR | 20110023060 | A | * | 3/2011 | B66B 31/02 |
| KR | 20110046740 | A | * | 5/2011 | B66B 31/02 |
| KR | 20120000195 | U | * | 1/2012 | |
| KR | 102240853 | B1 | * | 4/2021 | A61L 2/10 |
| WO | WO-2016083049 | A1 | * | 6/2016 | B65G 23/14 |

* cited by examiner

AUTOMATIC CONVEYOR AND AUTOMATIC CLEANING DEVICE FOR THE HANDRAIL BELT THEREOF

FOREIGN PRIORITY

This application claims priority to Chinese Patent Application No. 202211404390.X, filed Nov. 10, 2022, and all the benefits accruing therefrom under 35 U.S.C. § 119, the contents of which in its entirety are herein incorporated by reference.

FIELD OF THE INVENTION

The present invention relates to the field of automatic conveying devices. More specifically, the present invention relates to an automatic cleaning device for the handrail belt of an automatic conveying device, such as an escalator or a moving walkway.

BACKGROUND OF THE INVENTION

The handrail belts of automatic conveying devices, such as escalators and moving walkways, often need to be cleaned for dirt removal and sterilization, so as to prevent virus infection. The existing escalator cleaning devices generally employ manual cleaning or using external devices. For escalators, the addition of external devices may not meet the requirements of relevant standards. For example, when the escalator is cleaned using an external device, the escalator may need to stop carrying passengers. In addition, external devices may require manual installation and operation. Some escalator systems may have built-in cleaning devices, but they mainly employ dry cleaning by, for example, brushes.

SUMMARY OF THE INVENTION

The object of the present application is to solve or at least alleviate the problems existing in the prior art.

According to one aspect, an automatic cleaning device for a handrail belt of an automatic conveying device is provided, the automatic cleaning device comprising: a base; a first cleaning unit and a second cleaning unit mounted on the base, wherein the first cleaning unit and the second cleaning unit are arranged in a front and back way in a moving direction of the handrail belt; a cleaning liquid conveying device, for conveying cleaning liquid to the first cleaning unit or the second cleaning unit; and a controller configured to control the cleaning liquid conveying device to deliver the cleaning liquid to one of the first cleaning unit and the second cleaning unit that first comes into contact with the handrail belt based on the running direction of the handrail belt during a cleaning operation.

Optionally, in an embodiment of the automatic cleaning device, the first cleaning unit and the second cleaning unit are movably mounted on the base, wherein the first cleaning unit and the second cleaning unit are movable between an operating position and an idle position relative to the base driven by a drive mechanism. When in the operating position, the first cleaning unit and the second cleaning unit are in contact with the handrail belt, and when in the idle position, the first cleaning unit and the second cleaning unit are separated from the handrail belt.

Optionally, in an embodiment of the automatic cleaning device, the cleaning liquid conveying device is connected to a cleaning liquid tank.

Optionally, in an embodiment of the automatic cleaning device, the cleaning liquid conveying device comprises a main pipeline connected to the cleaning liquid tank, a drive pump on the main pipeline, a first branch and a second branch respectively connected to the first cleaning unit and the second cleaning unit, and a switching valve selectively connecting the first branch with the main pipeline or connecting the second branch with the main pipeline.

Optionally, in an embodiment of the automatic cleaning device, when performing a cleaning operation, the controller controls the drive pump to start operating, controls the drive mechanism to drive the first cleaning unit and the second cleaning unit to move to the operating position, and controls the switching valve so that the cleaning liquid is supplied to one of the first cleaning unit and the second cleaning unit that first comes into contact with the handrail belt. And, when stopping the cleaning operation, the controller controls the drive mechanism to drive the first cleaning unit and the second cleaning unit to move to the idle position, and controls the drive pump to stop operating.

Optionally, in an embodiment of the automatic cleaning device, the automatic cleaning device further comprises an ultraviolet sterilization module, which sterilizes the handrail belt when it passes therethrough.

Optionally, in an embodiment of the automatic cleaning device, the controller is configured to automatically perform the cleaning operation at a specific time interval, wherein each cleaning operation lasts for a predetermined time period.

Optionally, in an embodiment of the automatic cleaning device, the controller is configured to perform the cleaning operation when the automatic conveying device is at idle speed or in normal operation.

Optionally, in an embodiment of the automatic cleaning device, the drive mechanism comprises a drive motor and a screw and nut mechanism, the first cleaning unit and the second cleaning unit are mounted on a movable bracket that is movable relative to the base, and the drive motor and the screw and nut mechanism drive the movable bracket to move on the base, so as to synchronously drive the first cleaning unit and the second cleaning unit to move.

Optionally, in an embodiment of the automatic cleaning device, one of the first cleaning unit and the second cleaning unit that receives the cleaning liquid performs wet cleaning, and the other of the first cleaning unit and the second cleaning unit that does not receive the cleaning liquid performs dry cleaning, so as to remove the cleaning liquid remaining on the handrail belt during the wet cleaning process.

Optionally, in an embodiment of the automatic cleaning device, the first cleaning unit and the second cleaning unit comprise replaceable cloth-based wiping heads, and the cleaning liquid conveying device delivers the cleaning liquid to the wiping head of the first cleaning unit or the second cleaning unit.

An automatic conveying device is also provided, which is provided with an automatic cleaning device according to the various embodiments.

Optionally, in an embodiment of the automatic conveying device, the automatic conveying device is an escalator or a moving walkway, and the automatic cleaning device is arranged inside the housing of the automatic conveying device to clean the handrail belt in a reverse running section of the handrail belt.

The automatic cleaning device according to the embodiments of the present invention can clean the handrail belt of an automatic conveying device in an automatic, intelligent and convenient manner.

BRIEF DESCRIPTION OF THE DRAWINGS

With reference to the accompanying drawings, the disclosure of the present application will become easier to understand. Those skilled in the art would easily understand that these drawings are for the purpose of illustration, and are not intended to limit the protection scope of the present application. In addition, in the figures, similar numerals are used to denote similar components, where.

DETAILED DESCRIPTION OF EMBODIMENT(S) OF THE INVENTION

Figure 1:
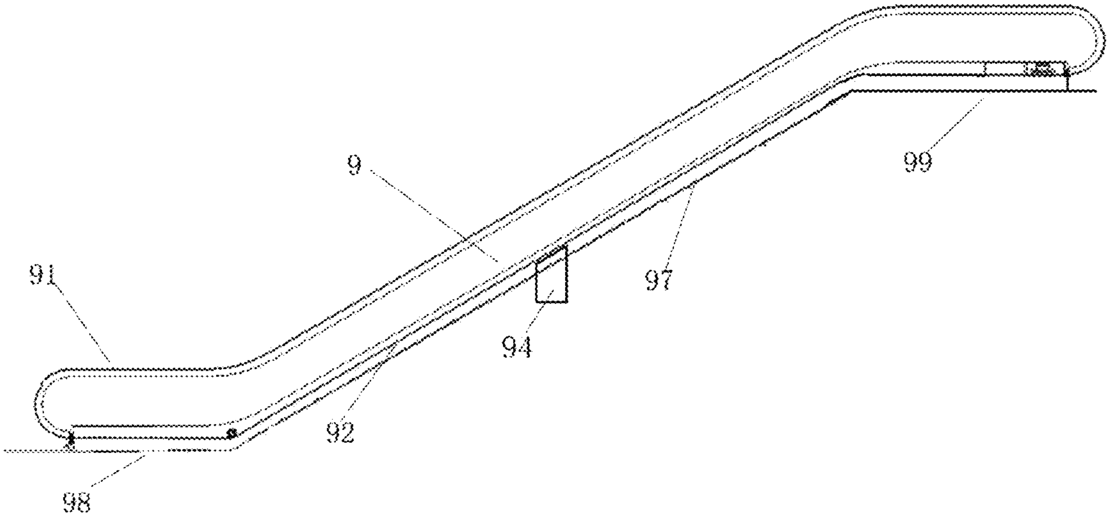
FIG. 1 is a structural schematic diagram of an escalator according to an embodiment of the present invention.

FIG. 1 shows an escalator 9, which is arranged between a first floor 98 and a second floor 99 higher than the first floor 98, and includes an inclined section 97. The escalator can be any known type of escalator that includes a handrail belt. The handrail belt forms a cycle, and includes at any time a forward running section 91 accessible to passengers and a reverse running section 92 hidden in the housing of the escalator. The handrail belt at the forward running section 91 has the same running direction as the steps of the escalator, and passengers may contact these parts of the handrail belt when taking the escalator. The escalator according to the embodiments of the present invention is provided with an automatic cleaning device 94 for cleaning the handrail belt thereof. The automatic cleaning device 94 can avoid, for example, the forward running section 91 of the handrail belt, so as to avoid affecting passengers taking the escalator. In some embodiments, the automatic cleaning device 94 can avoid complex structure positions such as the machine rooms on the first floor 98 and the second floor 99, and is fixed at the inclined section 97 of the escalator to clean the reverse running section 92 of the escalator handrail belt. Alternatively, the automatic cleaning device 94 can also be arranged at any other suitable position of the escalator. Alternately, the automatic cleaning device 94 can also be used for moving walkways, i.e., horizontally arranged step conveying devices. Escalators and moving walkways are collectively referred to as automatic conveying devices in the present invention.

With continued reference to FIGS. 2 to 5, an automatic cleaning device for a handrail belt of an automatic conveying device according to the various embodiments will be described. The automatic cleaning device comprises: a base 1; a cleaning module 100 mounted on the base, a sterilization module 2 and a cleaning liquid tank 4. The cleaning liquid tank 4 is arranged further away from the handrail belt than the cleaning module 100 and the sterilization module 2. In the illustrated embodiment, the cleaning module 100 and the sterilization module 2 are arranged in a front and back way in the running direction of the handrail belt of the escalator. A pair of guide wheels 13 can be arranged at the front and rear sides of the cleaning module 100 and the sterilization module 2.

Figure 2:
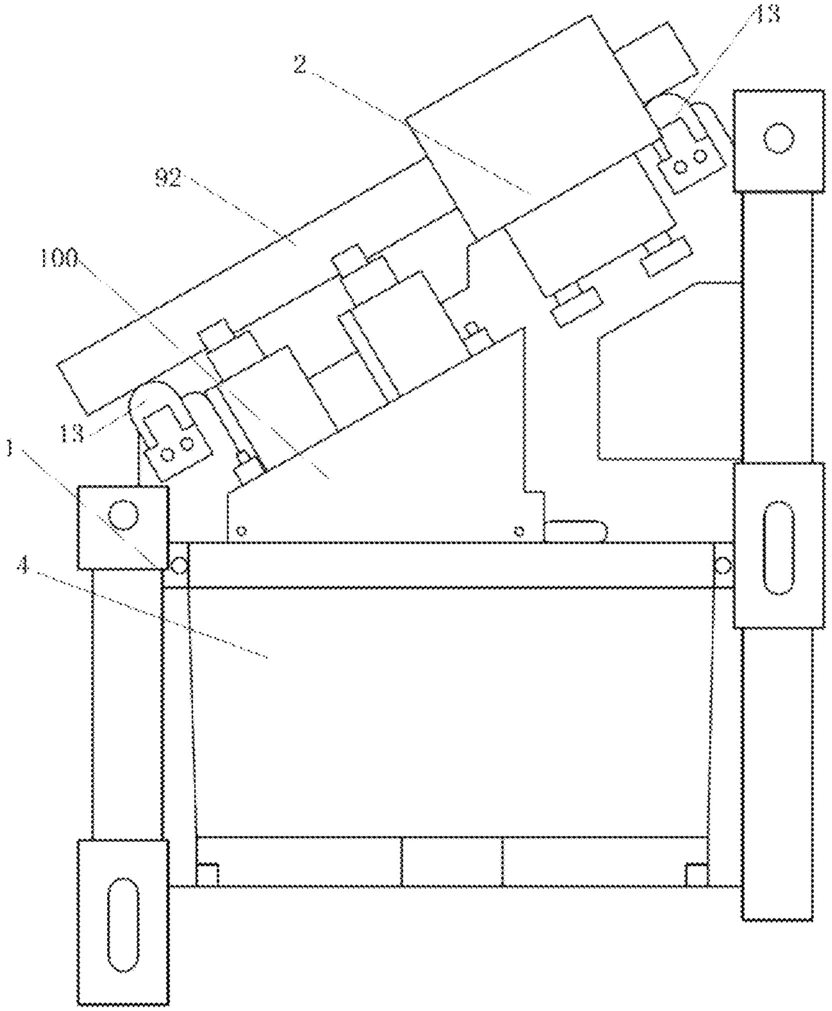
FIG. 2 is a side view of an automatic cleaning device according to an embodiment of the present invention.
Figure 3:
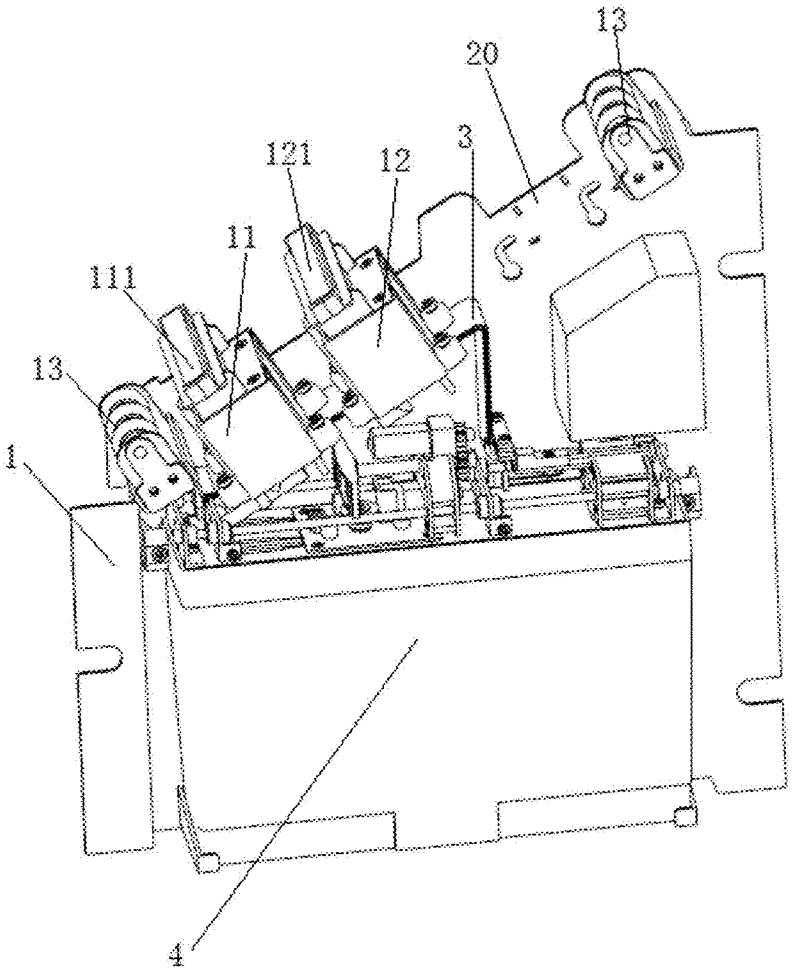
FIGS. 3 and 4 are respectively a perspective view and a side view of the internal structure of an automatic cleaning device according to an embodiment of the present invention.
Figure 4:
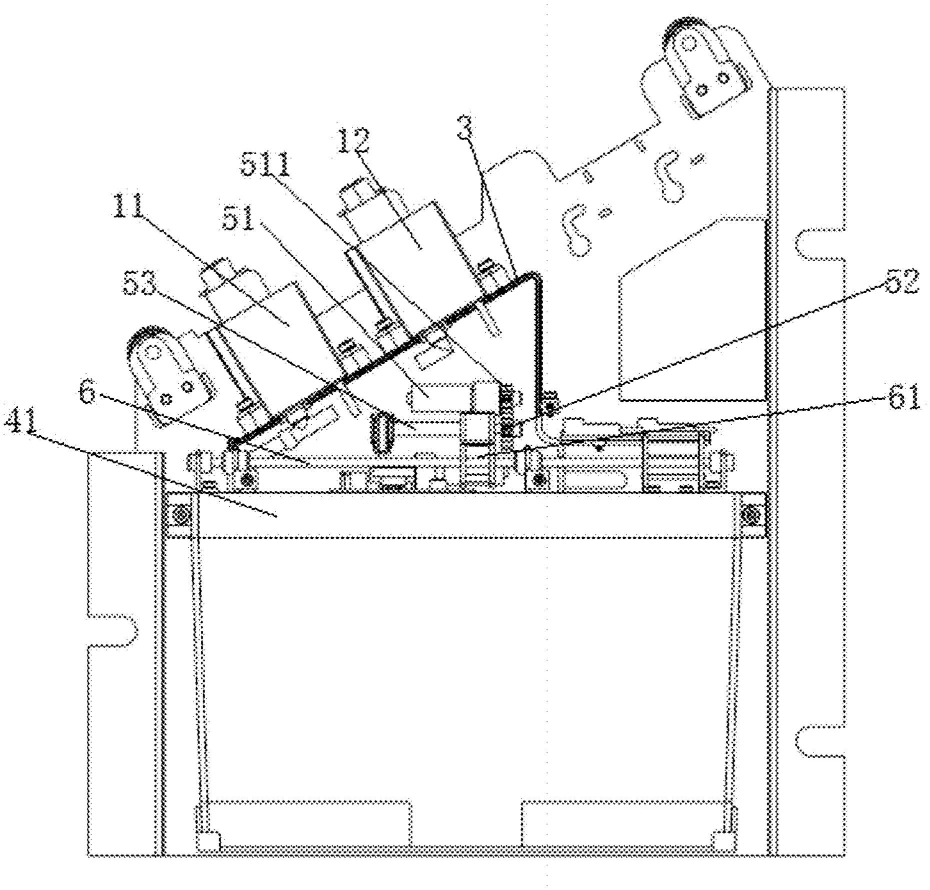

The housing of the cleaning module 100 is removed in FIGS. 3 and 4, so as to show the internal structure of the cleaning module 100 and the sterilization module 2 and the cleaning liquid conveying device are not depicted for clarity. The cleaning module 100 comprises a first cleaning unit 11 and a second cleaning unit 12. The first cleaning unit 11 and the second cleaning unit 12 are arranged in a front and back way in the moving direction of the handrail belt. Taking the case in FIG. 2 as an example, if the escalator goes up and the reverse running section 92 of the handrail belt goes down, the second cleaning unit 12 is in front and the first cleaning unit 11 is behind. On the contrary, if the escalator goes down and the reverse running section 92 of the handrail belt goes up, then the first cleaning unit 11 is in front and the second cleaning unit 12 is behind.

Figure 5:
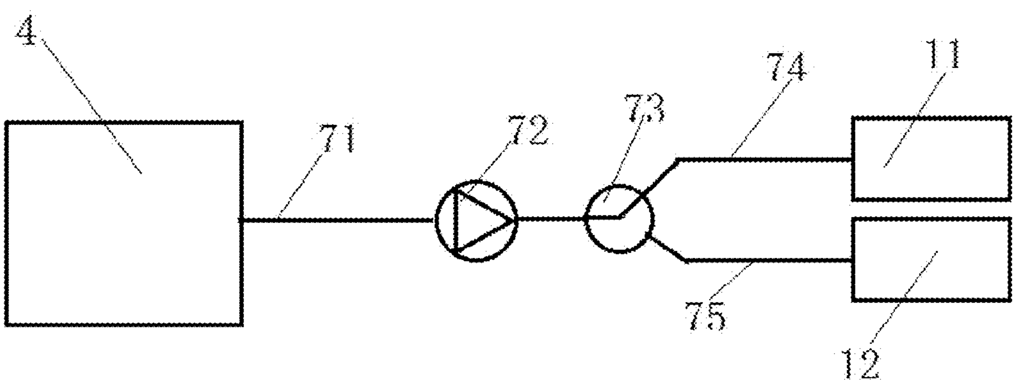
FIG. 5 is a structural schematic diagram of a cleaning liquid conveying device of an automatic cleaning device according to an embodiment of the present invention.

In addition, as shown schematically in FIG. 5, the cleaning liquid conveying device is arranged between the cleaning liquid tank 4 and the first cleaning unit 11 and the second cleaning unit 12. The cleaning liquid conveying device alternatively delivers the cleaning liquid to either the first cleaning unit 11 or the second cleaning unit 12. In an alternative embodiment, the cleaning liquid conveying device can be directly connected to the cleaning liquid source, while the cleaning liquid tank 4 is not necessarily to be arranged at this point. The cleaning liquid can be water or other suitable types of sterilization or disinfection cleaning liquids.

The automatic cleaning device 94 further comprises a controller configured to control the cleaning liquid conveying device to deliver the cleaning liquid to one of the first cleaning unit 11 and the second cleaning unit 12 that first comes into contact with the handrail belt during the cleaning operation based on the running direction of the handrail belt. The so-called "first come into contact with the handrail belt" refers to that a specific position of the handrail belt will pass through the first cleaning unit 11 and the second cleaning unit 12 in turn during the movement of the handrail belt. In some embodiments, one of the first cleaning unit and the second cleaning unit that receives the cleaning liquid, i.e., the one that first comes into contact, performs wet cleaning, and the other of the first cleaning unit and the second cleaning unit that does not receive the cleaning liquid, i.e., the one that later comes into contact, performs dry cleaning so as to wipe off the cleaning liquid remaining on the handrail belt during the wet cleaning process. Through this arrangement, one of the first cleaning unit 11 and the second cleaning unit 12 that first comes into contact with the handrail belt is responsible for wet wiping the handrail belt, while the other one is responsible for dry wiping the handrail belt to remove any cleaning liquid remaining on the handrail belt. Consequently, no matter the escalator runs in any direction, two steps of wet wiping and dry wiping can be realized to clean the handrail belt, thereby better cleaning the handrail belt.

In some embodiments, the first cleaning unit 11 and the second cleaning unit 12 are movably mounted on the base 1. In some embodiments, the first cleaning unit 11 and the second cleaning unit 12 include cloth-based replaceable wiping heads 111, 121, and the cleaning liquid conveying device delivers the cleaning liquid to the wiping head 111 of the first cleaning unit 11 or the wiping head 121 of the second cleaning unit 12 to wet the cloth therein. In some embodiments, the first cleaning unit 11 and the second cleaning unit 12 can move between an operating position and an idle position relative to the base 1 driven by the drive mechanism. In the operating position, the first cleaning unit 11 and the second cleaning unit 12 are in contact with the handrail belt 92, while in the idle position, the first cleaning unit 11 and the second cleaning unit 12 are separated from the handrail belt 92. Therefore, the first cleaning unit 11 and the second cleaning unit 12 only come into contact with the handrail belt when the cleaning operation is desired, without any impact on the automatic conveying device during normal operation.

As shown in FIG. 4, the first cleaning unit 11 and the second cleaning unit 12 are first mounted on a movable bracket 3. The drive mechanism comprises a drive motor and a screw and nut mechanism. More specifically, the drive mechanism comprises a drive motor 51 mounted on the movable bracket 3. The output shaft of the drive motor 51 includes a gear 511, which meshes with a gear 52 on the screw 53 of the screw and nut mechanism. The screw 53 is also mounted on the movable bracket 3. The movable bracket 3 is mounted in a horizontally movable manner on the base 1, for example, on the top platform 41 of the cleaning liquid tank 4. Specifically, the movable bracket 3 is connected to the ferrule on the horizontal guide rail 6 sleeved on the top platform 41. In addition, the nut part 61 of the screw and nut mechanism is fixed, such as fixed to the horizontal guide rail 6 on the top platform 41. Through this structure, when the drive motor 51 rotates, it drives the screw to rotate, thereby driving the movable bracket 3 to bring the first cleaning unit 11 and the second cleaning unit 12 to move horizontally between the operating position and the idle position. As shown in FIG. 4, the movable bracket includes an inclined plane and a vertical plane, and the drive motor and screw and nut mechanism are accommodated in the cavity formed by the inclined plane and vertical plane of the movable bracket, thus achieving a compact structure.

In some embodiments, as shown in FIG. 5, the cleaning liquid conveying device comprises a main pipeline 71 connected to the cleaning liquid tank 4, a drive pump 72 on the main pipeline 71, a first branch 74 and a second branch 75 respectively connected to the first cleaning unit 11 and the second cleaning unit 12, and a switching valve 73 that selectively connects the first branch 74 to the main pipeline 71 or connects the second branch 75 to the main pipeline 71. Through this arrangement, the cleaning liquid in the cleaning liquid tank 4 can be selectively delivered to the first cleaning unit 11 or the second cleaning unit 12. It should be understood that the cleaning liquid conveying device shown in FIG. 5 is only an example. In alternative embodiments, the switching valve 73 can also be replaced by solenoid valves arranged on the first branch 74 and the second branch 75. In other embodiments, there may be two independent paths respectively connected between the first cleaning unit 11 and the second cleaning unit 12 and the cleaning liquid tank 4, where each path may be configured with a solenoid valve. In alternative embodiments, the cleaning liquid conveying device can be connected to a cleaning liquid source with a certain pressure, and at this point, the drive pump can be omitted.

In some embodiments, when performing the cleaning operation, the controller controls the drive mechanism to drive the first cleaning unit 11 and the second cleaning unit 12 to move to the operating position, controls the drive pump 72 to work, and controls the switching valve 73 so that the cleaning liquid is supplied to one of the first cleaning unit 11 and the second cleaning unit 12 that first comes into contact with the handrail belt. And, when stopping the cleaning operation, the controller controls the drive mechanism to drive the first cleaning unit 11 and the second cleaning unit 12 to move to the idle position, and controls the drive pump 72 to stop operating.

In some embodiments, the sterilization module 2 can be an ultraviolet sterilization module. As shown in FIG. 2, the ultraviolet sterilization module is arranged before or after the first cleaning unit 11 and the second cleaning unit 12 in the moving direction of the handrail belt. In alternative embodiments, the sterilization module 2 can also be arranged between the first cleaning unit 11 and the second cleaning unit 12. The ultraviolet sterilization module sterilizes the handrail belt when it passes therethrough.

In some embodiments, the controller is configured to automatically perform a cleaning operation at a specific time interval, such as once every 24 hours, where each cleaning operation lasts for a predetermined time period, such as 5 minutes. In some embodiments, the controller is configured to perform an automatic cleaning operation when the escalator has no passengers and is at idle speed, at which time the handrail belt moves slowly. Alternatively, the controller is configured to perform a cleaning operation when the escalator is in normal operation, at which time the handrail belt moves relatively fast.

In addition, protection is also to be sought for an automatic conveying device, which is provided with an automatic cleaning device according to the various embodiments. The automatic conveying device is an escalator or a moving walkway, and the automatic cleaning device is arranged inside the automatic conveying device to clean the handrail belt in the reverse running section 92 of the handrail belt.

The specific embodiments described above are merely intended to describe the principles of the present application more clearly, wherein various components are clearly shown or described to facilitate the understanding of the principles of the present application. Those skilled in the art may, without departing from the scope of the present application, make various modifications or changes to the present application. Therefore, it should be understood that these modifications or changes should be included within the scope of patent protection of the present application.

What is claimed is:

1. An automatic cleaning device for a handrail belt of an automatic conveying device, the automatic cleaning device comprising:

a base;

a first cleaning unit and a second cleaning unit mounted on the base, wherein the first cleaning unit and the second cleaning unit are arranged in a front and back way in a moving direction of the handrail belt;

a cleaning liquid conveying device, for conveying cleaning liquid to the first cleaning unit or the second cleaning unit; and a controller configured to control the cleaning liquid conveying device to deliver the cleaning liquid to only one of the first cleaning unit and the second cleaning unit that first comes into contact with the handrail belt based on a running direction of the handrail belt during a cleaning operation, such that in a first handrail belt direction the first cleaning unit receives the cleaning liquid and the second cleaning unit does not receive the cleaning liquid and in a second handrail belt direction opposite to the first handrail belt direction the second cleaning unit receives the cleaning liquid and the first cleaning unit does not receive the cleaning liquid.

2. The automatic cleaning device according to claim 1, wherein the first cleaning unit and the second cleaning unit are movably mounted on the base, and the first cleaning unit and the second cleaning unit are movable between an operating position and an idle position relative to the base driven by a drive mechanism, and wherein, when at the operating position, the first cleaning unit and the second cleaning unit are in contact with the handrail belt, and when at the idle position, the first cleaning unit and the second cleaning unit are separated from the handrail belt.

3. The automatic cleaning device according to claim 1, wherein the automatic cleaning device further comprises a cleaning liquid tank, and the cleaning liquid conveying device is connected to the cleaning liquid tank.

4. The automatic cleaning device according to claim 1, wherein the cleaning liquid conveying device comprises a main pipeline connected to the cleaning liquid tank, a drive pump on the main pipeline, a first branch and a second branch respectively connected to the first cleaning unit and the second cleaning unit, and a switching valve selectively connecting the first branch to the main pipeline or connecting the second branch to the main pipeline.

5. An automatic cleaning device for a handrail belt of an automatic conveying device, the automatic cleaning device comprising:

a base;

a first cleaning unit and a second cleaning unit mounted on the base, wherein the first cleaning unit and the second cleaning unit are arranged in a front and back way in a moving direction of the handrail belt;

a cleaning liquid conveying device, for conveying cleaning liquid to the first cleaning unit or the second cleaning unit; and a controller configured to control the cleaning liquid conveying device to deliver the cleaning liquid to one of the first cleaning unit and the second cleaning unit that first comes into contact with the handrail belt based on a running direction of the handrail belt during a cleaning operation;

wherein the cleaning liquid conveying device comprises a main pipeline connected to the cleaning liquid tank, a drive pump on the main pipeline, a first branch and a second branch respectively connected to the first cleaning unit and the second cleaning unit, and a switching valve selectively connecting the first branch to the main pipeline or connecting the second branch to the main pipeline;

wherein, when performing a cleaning operation, the controller controls the drive pump to start operating, controls the drive mechanism to drive the first cleaning unit and the second cleaning unit to move to the operating position, and controls the switching valve so that the cleaning liquid is supplied to one of the first cleaning unit and the second cleaning unit that first comes into contact with the handrail belt, and when stopping the cleaning operation, the controller controls the drive mechanism to drive the first cleaning unit and the second cleaning unit to the idle position, and controls the drive pump to stop operating.

6. The automatic cleaning device according to claim 1, wherein the automatic cleaning device further comprises an ultraviolet sterilization module that sterilizes the handrail belt when it passes therethrough.

7. The automatic cleaning device according to claim 1, wherein the controller is configured to automatically perform the cleaning operation at a specific time interval, where each cleaning operation lasts for a predetermined time period.

8. The automatic cleaning device according to claim 1, wherein the controller is configured to perform the cleaning operation when the automatic conveying device is at idle speed or in normal operation.

9. The automatic cleaning device according to claim 1, wherein the drive mechanism comprises a drive motor and a screw and nut mechanism, the first cleaning unit and the second cleaning unit are mounted on a movable bracket that is movable relative to the base, and the drive motor and the screw and nut mechanism drive the movable bracket to move on the base, so as to synchronously drive the first cleaning unit and the second cleaning unit to move.

10. The automatic cleaning device according to claim 1, wherein one of the first cleaning unit and the second cleaning unit that receives the cleaning liquid performs wet cleaning, and the other of the first cleaning unit and the second cleaning unit that does not receive the cleaning liquid performs dry cleaning, so as to remove the cleaning liquid that remains on the handrail belt during the wet cleaning.

11. The automatic cleaning device according to claim 1, wherein the first cleaning unit and the second cleaning unit comprise replaceable cloth-based wiping heads, and the cleaning liquid conveying device delivers the cleaning liquid to the wiping head of the first cleaning unit or the second cleaning unit.

12. An automatic conveying device, wherein the automatic conveying device is provided with an automatic cleaning device according to claim 1 comprising:

a base;

a first cleaning unit and a second cleaning unit mounted on the base, wherein the first cleaning unit and the second cleaning unit are arranged in a front and back way in a moving direction of the handrail belt;

a cleaning liquid conveying device, for conveying cleaning liquid to the first cleaning unit or the second cleaning unit; and a controller configured to control the cleaning liquid conveying device to deliver the cleaning liquid to only one of the first cleaning unit and the second cleaning unit that first comes into contact with the handrail belt based on a running direction of the handrail belt during a cleaning operation, such that in a first handrail belt direction the first cleaning unit receives the cleaning liquid and the second cleaning unit does not receive the cleaning liquid and in a second handrail belt direction opposite to the first handrail belt direction the second cleaning unit receives the cleaning liquid and the first cleaning unit does not receive the cleaning liquid.

13. The automatic conveying device according to claim 12, wherein the automatic conveying device is an escalator or a moving walkway, and the automatic cleaning device is arranged inside a housing of the automatic conveying device to clean the handrail belt in a reverse running section of the handrail belt.

* * * * *